United States Patent
Altrichter et al.

(10) Patent No.: US 6,509,147 B1
(45) Date of Patent: Jan. 21, 2003

(54) METHOD FOR THERAPEUTIC IMMUNMODULATION OF PLASMA

(75) Inventors: Jens Altrichter, Kavelstorf (DE); Jens Freytag, Rostock (DE); Steffen Mitzner, Rostock (DE); Jan Stange, Rostock (DE)

(73) Assignee: Teraklin Aktiengessellschaft (DE)

( * ) Notice: Subject to any disclaimer, the term of this patent is extended or adjusted under 35 U.S.C. 154(b) by 0 days.

(21) Appl. No.: 09/352,987

(22) Filed: Jul. 14, 1999

(30) Foreign Application Priority Data

Jul. 16, 1998 (DE) ............................................ 19831873

(51) Int. Cl.[7] ................................................ C12N 5/00
(52) U.S. Cl. ........................... 435/2; 435/325; 435/315; 435/289.1; 210/602; 424/93.7; 424/530
(58) Field of Search ................................. 435/325, 395, 435/2, 289.1, 70.1, 70.4, 70.3; 210/602; 424/530, 937

(56) References Cited

U.S. PATENT DOCUMENTS

| 5,087,569 A | * | 2/1992 | Gabay et al. |
| 5,230,886 A | * | 7/1993 | Treon et al. |
| 5,270,192 A | * | 12/1993 | Li et al. |
| 5,679,775 A | * | 10/1997 | Boos et al. |
| 5,976,870 A | * | 11/1999 | Park |
| 6,068,775 A | * | 5/2000 | Custer et al. |

FOREIGN PATENT DOCUMENTS

| DE | 693 03 779 T2 | 1/1997 |
| WO | WO 93/16171 | 8/1993 |

* cited by examiner

Primary Examiner—Leon B. Lankford, Jr.
(74) Attorney, Agent, or Firm—Paul & Paul

(57) ABSTRACT

A process and set-up of therapeutic immunomodulation is provided for medicine. Many illnesses (i.e. Sepsis) are, among other things, characterized by a disruption of the immune system. In spite of previous therapies using antibiotics, the mortality rate is still very high. The administration of individual cytokins has not yet resulted in any convincing results. The use of cells in an extra-corporal circulation that can adsorb or self-release immunomodulatory effect substances is a completely new type of complex therapeutic approach to such illnesses, which leads to an improvement in the health of the affected patients.

6 Claims, No Drawings

METHOD FOR THERAPEUTIC IMMUNMODULATION OF PLASMA

BACKGROUND OF THE INVENTION

The current knowledge regarding the course and the pathogenesis of a sepsis comes in large part from studies on the interaction between gram-negative bacteria and the human organism (Chest 1992; 101; 1644–1655). The primary agents for introducing a sepsis cascade accordingly produce bacterial endotoxins, a group of lipopolysaccharides from the cell wall of gram-negative bacteria. (Reviews Infect. Dis. 1983; 5; 733–747). Endotoxins, possibly the most potent fever-producing substances of all (pyrogens), activate above all monocytes and endothelial cells. The immune system is activated through the release of mediators or, as the case may be, the development of adhesive molecules, preparing a leukocytic suppression. This leads to a migration of the leukocytes into tissues with high chemotoxin content (site of local inflammation). If the local cause can be eliminated, then the inflammation process is impeded. If over a longer time period, either intermittently or continuously, this leads to an excessive influx of bacteria, endotoxins or other antigen-like acting cell products into the blood, then the useful defense reaction by monocytes and endothelial cells changes into an autoaggressive process with severe circulation dysfunction, secondary organ failures, coagulation disruptions (DIC), etc.; a sepsis (with positive proof of causative agent) or, as the case may be, a systemic inflammatory response syndrome (SIRS, no provable cause) develop and cause death in up to 30% of the cases where a simple sepsis is involved and up to 90% in patients where septic shock is involved. (Sepsis. An interdisciplinary challenge. Berlin, Heidelberg, New York: Springer Verlag, 1989).

Gram-positive causes of the genesis of sepsis have in recent years increasingly become an object of research study. Countless studies deal with the increased incidence of gram-positive sepsis in the last decade. Statistics show that now already 30 to 40% of all cases of sepsis can be traced back to gram-positive causes (Am J. Med. 1991; 91 (suppl. 3B): 72–89).

The treatment of bacterial sepsis in intensive-care medical centers is made additionally difficult because of increasing resistance to antibiotics.

Currently, sepsis is viewed as a multi-phasic illness in which a so-called hyperinflammatory phase with an excessive outpouring of pro-inflammatory cytokines, such as for example tumor-necrosis factor alpha (TNF alpha) or various interieukins (i.e. interleukin-1 and interieukin-6), joins with the germ-outpouring phase. Due to negative feedback, the course as it continues leads to an overflow change in anti-inflammatory cytokines (transformative growth factor beta=TGF beta, interleukin-4, interleukin-10, interleukin-13) and thus to the so-called immunoparalysis phase, which eventually leads to the patient's death (Internist 1997; 38; 541–552). A clear definition of the individual phases based on concrete para-clinical values has, however, not yet been established.

Until today, the causal treatment of bacterial sepsis is possible only in stages. Next to antibiotic therapy, hopes rest on the application of anti-inflammatory substances that are currently being tested for their effects on gram-negative sepsis. (Nature. 1990; 348: 550–552, FASEB J. 1991; 5: 338–343). Some studies on this have already been completed and have until now yielded more often than not disappointing results. Thus, neither antibodies directed against the endotoxin lipid A (N. Engl. J. Med. 1991; 324; 429–436, JAMA 1991; 266; 1097–1102) nor anti-cytokine therapies against the tumor necrosis factor alpha (Crit. Care Med. 1993: 21; 318–327, JAMA 1995; 273; 934–941) nor interieukin-1 (JAMA 1994; 271; 1836–1842) could contribute to a reduction in the overall mortality rate. It seemed, however, that patients with very high cytokine levels at least partially benefited (Crit. Care Med. 1993; 21; 318–327, Crit. Care Med. 1996; 24; 733–742). The studies are, however, characterized by the large heterogeneity of the patient groups as well as the insufficient assignment until now of clinical studies on the course of sepsis.

A new approach is the use of pro-inflammatory cytokines (interferon gamma) in the immunoparalysis phase, which seemed promising in the first non-random studies, but which, however, still showed an over 30% mortality rate (Nature Medicine 1997; 3; 678–681). Legally registered patents for immunomodulatory substances, such as for example, some of the above described cytokine antagonists (WO 9406431 A1, U.S. Pat. Nos. 5,585,486, 5,585,357, 5,565,430, 5,552,400), mistel-lektine (DE 4221836 A1), fosfomycin (JP 09183730 A), macrocyclical substances (U.S. Nos. 5,527,907, 5,541,189, 5,541,193, 5,561,139, 5,561,140) or bacterial extracts (WO 8909607 A, EP 363491 A1). None of these approaches could show decisive therapeutic gains in sepsis therapy.

The therapeutic approaches known up until now were primarily implemented through in vivo administration of antibodies directed against cytokines or other cytokine-binding protein preparations and have produced no or only little therapeutic value. (Internist 1997; 38; 541–552, cf. 2, State of the Methodology).

Conditions of hyperinflammation or immunoparalysis lead to an increase in the blood plasma concentrations of a number of immunodeficient substances such as, for example, cytokines, which in part significantly disturb the processes of infection defense. The obliteration or addition of a single cytokine has until now not been a convincing therapeutic success. Rather, in demand is the useful removal of too-high concentrations of individual cytokines as well as the substitution of other cytokines that are present in too-diminished concentrations to stabilize the disrupted immune system.

SUMMARY OF THE INVENTION

The complexity of the problem of variable cytokine concentrations requires on the one hand sensitive measurement, on the other hand, however, it also requires the ability to quickly substitute the cytokines. However, because of the time delay in determining the cytokine concentration, substitution therapies in the form of injections/infusions can in the future only make a limited contribution to the solution. Constituting a new therapy is the use of cells, which, with their specific surface receptors, adsorb selectively and thus withdraw from circulation, but which, on the other hand, can also even form and release the underrepresented cytokines or other immunomodulatory effective molecules in the blood.

DETAILED DESCRIPTION OF THE INVENTION

Blood is drawn from a patient via a cannula penetrating a blood vessel and a connected tube system. The blood is then simultaneously or subsequently fed to an appropriate plasma separator, and is separated by filtration or differential centrifugation into corpuscular components (among others, blood cells) and blood plasma (plasmapherese). The blood plasma or blood plasma components is afterwards simultaneously or subsequently conducted through a bioreactor containing the immunomodulatory cells (i.e. vitamin D stimulated HL60 cells). These bioreactor cells bind immunomodulatory substances to specific surface receptors (i.e. they bind HL60 cytokines such as interferon gamma and growth factors such as granulocyte colony stimulatory factor) and through this lower their concentration in plasma. But, on the other hand, they self-release immunomodulatory substances as a reaction to external stimuli (i.e. release stimulated cells after incubation with opsonized zymosan interleukin 6 and tumor necrosis factor alpha), concentrations of which hereby increase in bioreactor elutriate or plasma. Through an appropriate process like cell-retaining systems (i.e. cell filtration), it is found that the cells are completely retained in the bioreactor. The bioreactor elutriate is afterwards reunited with the corpuscular blood components and re-infused into the patient. The corpuscular blood components can be reinfused into the patient, diluted or undiluted into appropriate solutions, separately or in an appropriate mixture with the processed blood plasma components.

For example, lab rats that were treated with *E. coli* bacteria survived significantly longer if the plasma was incubated with HL60 cells. In this regard, on the one hand a release of cytokines through HL60 cells could be proven. On the other hand, the treated animals' own cytokine levels were significantly lower in, for example, tumor necrosis factor alpha. The invention as described results, for the first time, in a causal therapeutic approach to the disruption of the body's own immune system regulation.

The use of cells that, on the one hand, very sensitively detect concentrations of immunomodulatory substances through adsorption of specific surface receptors and, on the other hand, release immunomodulatory effective substances, present a complex regulating mechanism that is suited for improving the disruption of the body's own immune system regulation arising in the course of a severe infection. The use of the invention's technical set-up ensures at all times the highest possible safety level for the patient. Because of the type of implementation of the technical set-up, a barrier between the patient's cells and the bioreactor cells is ensured at all times.

Examples of immunomodulatory cells are vitamin D stimulated HL60 cells, leukocyte cells, leukocyte cells derived from a human cell line, haematopoietic stem cells, cells obtained from haematopoietic stem cells through differentiation, hepatocytes, and endothelial cells. Examples of immunomodulatory effective substances are growth factors, endotoxins, such as lipopolysaccharides from the cell wall of gram-negative bacteria, and cytokines, preferably interferons and interleukins such as interferon gamma, interleukin 4, interleukin 10, and interleukin 13, tumor necrosis factor beta, and transforming growth factor beta.

We claim:

1. A method for increasing and/or decreasing the concentrations of immunomodulatory effective substances in blood plasma, the method comprising the steps of:

separating blood into corpuscular components and blood plasma or blood plasma components;

adding the blood plasma to a bioreactor containing immunomodulatory cells;

contacting the blood plasma in the bioreactor with the immunomodulatory cells, wherein the cells have specific surface receptors and are able to decrease the concentrations of immunomodulatory effective substances in the plasma by adsorption of such substances at the specific receptors, and the cells are able to increase the concentrations of immunomodulatory effective substances in the plasma by releasing immunomodulatory effective substances into the plasma, separating the plasma from the immunomodulatory cells and removing it from the bioreactor, wherein the immunomodulatory cells are selected from the group consisting of endothelial cells, leukocytes, cells obtained from haematopoietic stem cells through differentiation, and cell lines derived from the aforementioned cells, and wherein the immunomodulatory effective substances belong to the group consisting of growth factors, endotoxines, and cytokines.

2. The method of claim 1, wherein the cytokines are interferons and interleukines.

3. The method of claim 1, wherein the immunomodulatory effective substances belong to the group consisting of interferon gamma, interleukine 1, interleukine 2, interleukine 4, interleukine 6, interleukine 10, interleukine 13, tumor necrosis factor alpha, and transforming growth factor beta.

4. The method of claim 1, wherein temperature, supplying of gas, and supplying of nutrients to the cells in the bioreactor is regulated.

5. The method of claim 1, wherein the blood plasma is separated from the cells using a cell-retaining system.

6. The method of claim 5, wherein the cell-retaining system is a cell filter or a centrifuge.

* * * * *

UNITED STATES PATENT AND TRADEMARK OFFICE
CERTIFICATE OF CORRECTION

PATENT NO. : 6,509,147 B1
DATED : January 21, 2003
INVENTOR(S) : Jens Altricher et al.

It is certified that error appears in the above-identified patent and that said Letters Patent is hereby corrected as shown below:

Column 1,
Line 51, delete "interieukins" and insert -- interleukins --
Line 51, delete "and interieukin-6)" and insert -- and interleukins-6) --

Column 2,
Line 6, delete "interieukin-1" and insert -- interleukin-1 --

Signed and Sealed this

Eighth Day of April, 2003

JAMES E. ROGAN
*Director of the United States Patent and Trademark Office*